US00PP09708P

United States Patent [19]

Sherman

[11] Patent Number: Plant 9,708

[45] Date of Patent: Nov. 26, 1996

[54] APPLE TREE 'FLA. 90-3'

[76] Inventor: Wayne B. Sherman, Horticultural Sciences Dept.-Fifield Hall-Univ. Florida, Gainesville, Fla. 32611

[21] Appl. No.: 522,983

[22] Filed: Sep. 5, 1995

[51] Int. Cl.[6] ..... A01H 5/00

[52] U.S. Cl. ..... Plt./34.1

[58] Field of Search ..... Plt./34.1

*Primary Examiner*—James R. Feyrer

[57] ABSTRACT

This invention termed, Fla. 90-3, is a new and distinct apple tree (*Malus xdomestica* Borkh) adapted to subtropical climates with mild winters. It was derived in the breeding attempt to obtain a low winter chilling requirement dessert apple, ripening one week before Anna ripens, with high fruit quality. The tree is a seedling of known parentage, [(NJ38× Anna)$F_2$], planted in 1987 in the University of Florida fruit breeding orchard near Gainesville, Fla. The tree was selected and tested in Fla. 90-3. Fruit taste much sweeter (Brix 13.0 to 14.0) and less sour (acidity) than Anna cultivar.

2 Drawing Sheets

BACKGROUND OF THE INVENTION

The cultivar, Fla. 90-3, is a new apple invention with a distinct low-chilling and dormancy requirement. This present invention resulted from our breeding efforts to produce deciduous tree fruits adapted to mild winters of subtropical climates. Contrast is made to Anna, the standard apple cultivar of low winter cold requirement that is adapted and grown throughout subtropical climates of the world.

ORIGIN OF THE INVENTION

Fla. 90-3 apple tree (genotype) was originated by the breeders in the tree fruit breeding plots at the University of Florida, located at Gainesville, Fla. N.J. 38 (seed parent) was hybridized by Anna (pollen parent) in 1975 resulting in 4 selected siblings which were planted in isolation from other apples and permitted to fruit. Seed from fruit of the 4 selections were collected in 1986 to form a bulked polycross. Resulting seedlings from the polycross were planted in 1987 in university orchard evaluation plots at Gainesville, Fla. 90-3 was selected in 1990 and has been tested in Fla. 90-3. This invention has been propagated asexually by grafting onto standard seedlings and on MM106 rootstock as a uniform cultivar and is found to be adapted to mild winter climates as occurs in subtropical conditions. The grafted scions have retained the described characteristics of the fruiting trees. The asexual reproduction of this tree was performed at the above identified University facilities.

SUMMARY OF THE INVENTION

Fla. 90-3 apple tree is a low-chilling, winter dormancy requirement (estimated chilling requirement equivalent to Anna apple or about 300 chill units) and bears early ripening sweet and low acid fruit. Trees of Fla. 90-3 bloom with Anna apple at Gainesville but ripen in early June about a week before Anna. Fruit tast much sweeter than Anna and are noticeably lower in sourness (acidity), even when green ripe. Fruit range 20 to 30% red overcolor and have a green ground color compared to 50% for Anna and are about the same size (120 g or 6.5 cm diameter). Fruit shape is round-conic. Fruit are uniform in shape and size and mature in about 105 to 110 days after full bloom. Trees produce a moderately vigorous semi-spreading tree with good crotch angles with a simispur-type bearing habit.

Based on field observations, Fla. 90-3 is highly resistant to fire blight incited by *Erwinia amylovora* (Burr.) Winalow and has moderate resistance to powdery mildew incited by *Podosphaera leucotricha* (Ell. & Ev.) Salm.

The tree and fruit of Fla. 90-3 may vary in slight details due to variations in soil types, cultural practices, and climate conditions. The present botanical description is that of the cultivar grown under the ecological conditions prevailing at Gainesville, Fla.

BRIEF DESCRIPTION OF THE FIGURES OF THE DRAWING

The color photographic drawing of this disclosure consists of two Figures, as nearly true as is reasonbly possible to make in color illustrations of this type. The Figures show, respectively.

DETAILED DESCRIPTION of Fla. 90-3

Figure 1:
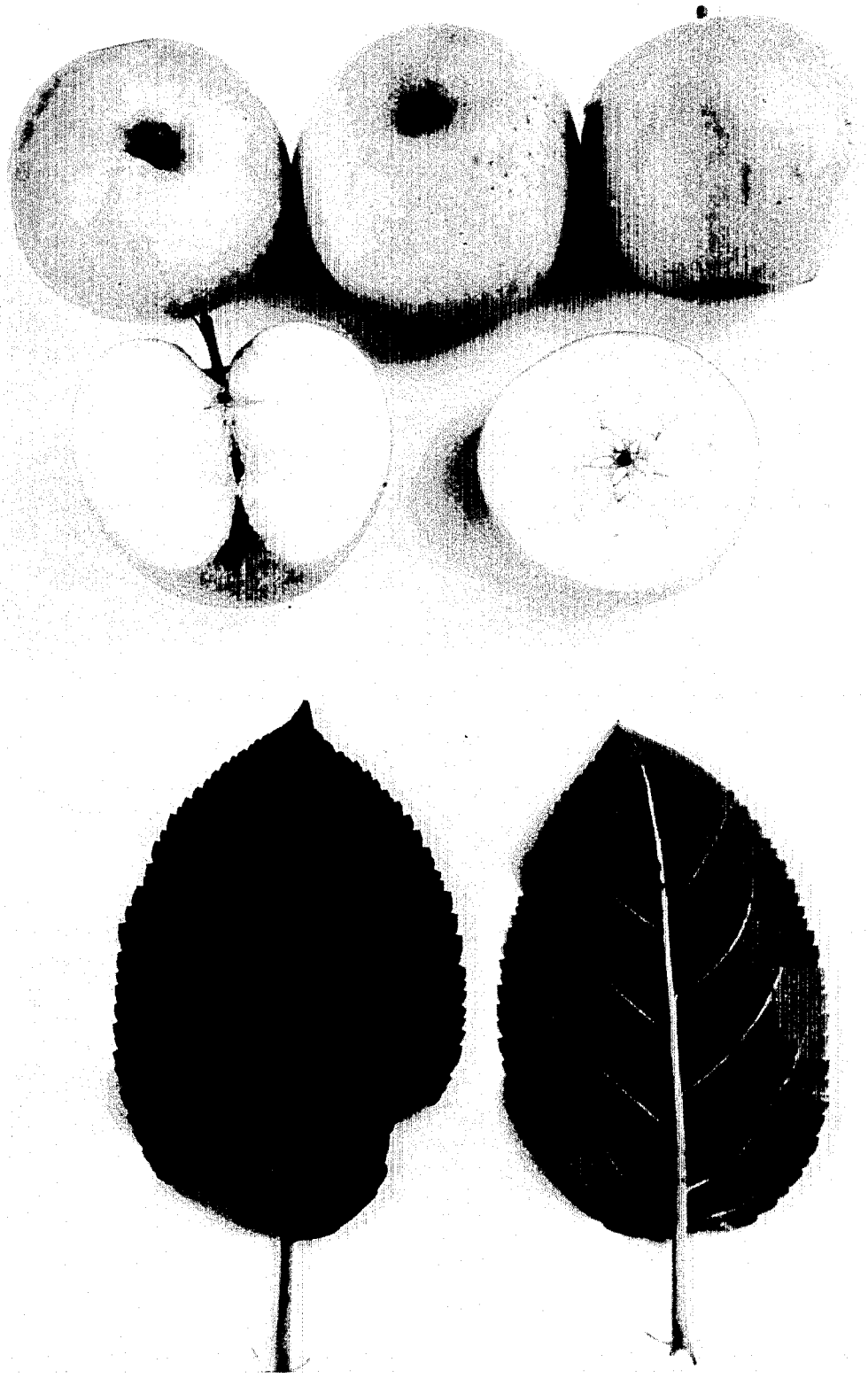
FIG. 1 depicts at the top, a row of typical whole specimens of fruit produced by this tree with the top left specimen oriented to show the stem end of the fruit, the top center fruit being positioned to show the blossom end of the fruit, and the specimen on the right placed to show the fruit in side view. These specimens reflect the external characteristics of skin ground color and over-color, pattern of over-color, lenticels, stem, calyz and basin characteristics. Below the top row, samples of sectioned fruit are shown with the specimen on the left being sliced on the core axis of the fruit to show the flesh coloration, core lines, calyx tunnel, and fruit stem in close range. The specimen on the right has been bisected to show the fruit internal characteristics in cross section, to indicate flesh texture, core lines, carpels and seed. At the bottom of FIG. 1, on the left, the top surface of a typical mature leaf is shown with the leaf petiole remaining and the stipules attached. On the bottom right, a similar leaf is shown with the bottom surface exposed; these samples having margins, coloration and venation characteristic of this tree.

The following is a detailed botanical description of the new and distinct variety of scion apple tree Fla. 90-3 with flowers, fruit, and tree as base on observations near Gainesville, Fla. with color descriptions according to "A Dictionary of Color", by Maerz and Paul published by McGraw Hill Book Co., Inc., 1930. The present apple tree, Fla. 90-3, including flowers and fruit may vary in slight detail due to climatic, soil conditions, and cultural practices under which the variety may be grown.

FLOWERS

Corolla: Average of 40 mm in diameter at anthesis

Petals: Petal color day prior to opening spinel red—plate 3, lines 5H fading to whitish plate 3 line 1C. There are 16 to 20 anthers per flower which are cream plate 9, line 2D. Petals average 19 mm long and 13 mm wide. Young leaves at 40 mm long and 25 mm wide appearing with open flowers from mixed buds are Brunswick green—(plate 22, line 10L). Flower color, shape, and size are similar to Anna.

FRUIT

Shape: Round-conic.

Size: Average diameter 6.5 cm and 120 g weight.

Color: Ground color shadow green (plate 20, line J3) with 20 to 30% reddish bluish (plate 4, lines L7 to 10) on sun-exposed cheek.

Skin: Smooth, light bloom, medium thickness, and conspicuous lenticels.

Stem: Medium size and thickness.

Basin: Medium depth and breath, rounded.

Calyx: Persistent, recurred.

Core lines: Top shaped.

Core: Median, closed.

Carpels: Emarginate at stem end, acuminate at distal end.

Seeds: Full complement, acute.

FLESH

Texture: Crisp, not melting, medium grained, moderate browning upon exposure to air.

Quality: Sweet, low acidity, rich, full flavor, very good for season.

Color: White at maturity, (plate 2, line 7A).

Maturity season: Ripens early June at Gainesville, Fla., a week before Anna or about 105 to 110 days after full bloom.

Use: Early summer dessert apple.

TREE

Growth habit: Moderate vigor with round semi-spreading top. Semi-spur type bearing habit. Very precocious, bearing in second-year growth on spurs and terminals.

Leaves: Obovate, acuminate at tip, obtuse at base, serrate edges. Length 9.4 cm, width 5.5 cm, petiole 2.7 cm with 2 stipules at base 3–4 mm. Length to width ratio=1.7.

Pruning/training requirements: Vigorous growth on young trees may require heading. Should be trained as trees of standard semi-spur cultivars.

Branch angles: Desirable branch angles, 70 to 90 degrees with little tendency for back inclusions in crotch.

Pollination: Requires cross pollination for optimum yields of uniform fruit shape. Cross-pollinates with Anna.

Productivity: Moderately productive.

Fruit thinning: Will require thinning to achieve optimum size.

Figure 2:
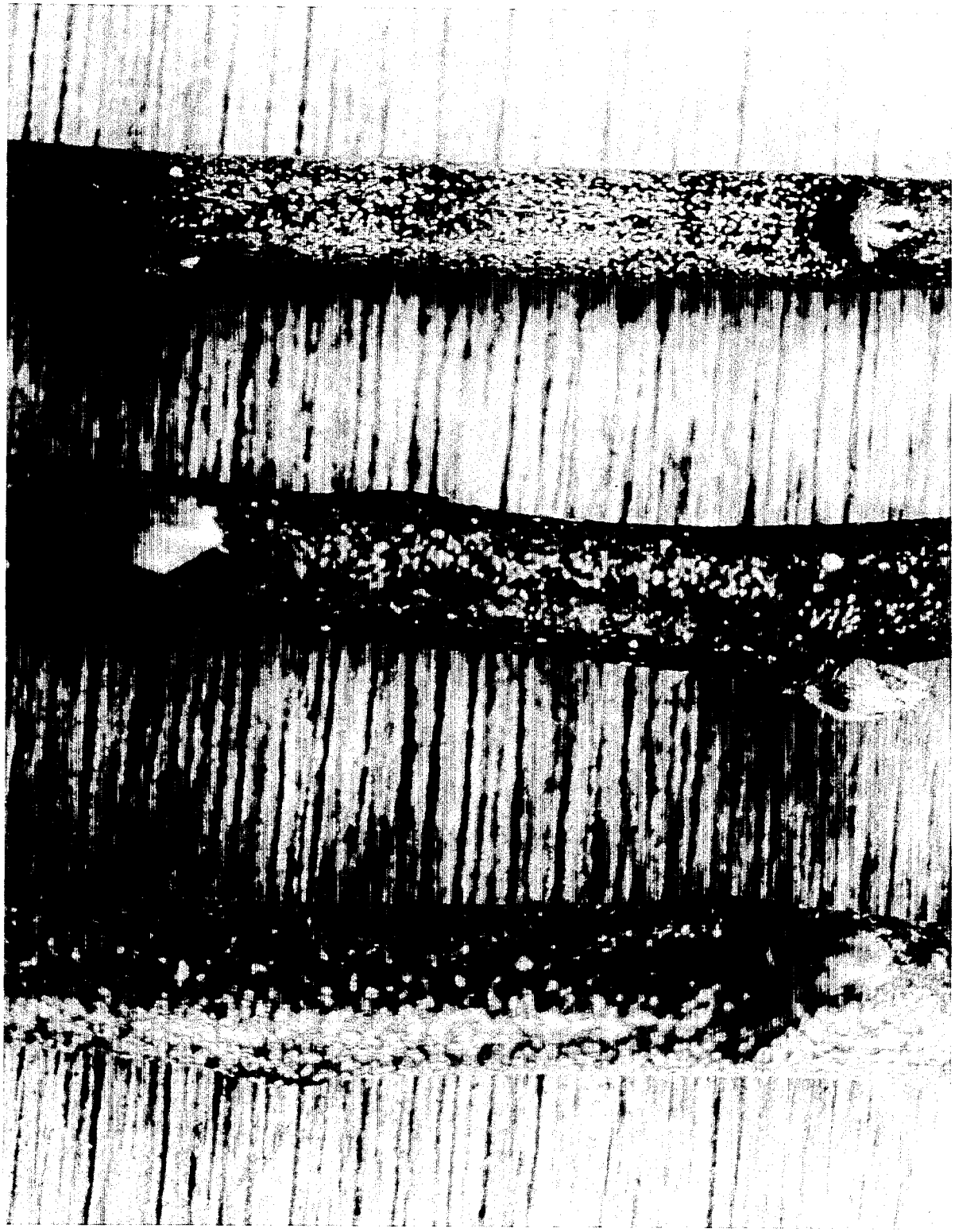
FIG. 2 shows stems of different maturity. The top two stems are newly formed and the bottom stem shows the coloration of an older stem with the faded lentical color. This photograph depicts the color of newly formed bark, the size, density, shape and orange color of lenticels, axillary bud size, shape and tomentum, and leaf scale scars characteristic of this tree.

Bark: Current-year stems in winter are reddish on sun-exposed surface, greenish on underside. Lenticels on one-year wood are raised and most numerous toward base with orange tent fading to white upon sun exposure (FIG. 2), similar to Anna, a unique characteristic of few apple cultivars.

I claim:

1. A new and distinct apple tree cultivar as illustrated and described, characterized by a low-chilling requirement and early-ripening fruit having sweet, low acid flesh and good dessert quality based on flavor and crisp flesh. In comparison to Anna, Fla. 90-3 tastes sweeter with much less acid and ripens about 1 week earlier with less red skin color.

* * * * *